United States Patent
Mazlin et al.

[11] Patent Number: 6,132,005
[45] Date of Patent: Oct. 17, 2000

[54] DETECTING SEAM BOUNDARY USING PICK SOUND

[75] Inventors: John Gordon Mazlin, Denistone; David John Mazlin, Ashfield; Brian Marston, Meadowbank, all of Australia

[73] Assignee: Tangential Technologies PTY, Parramatta, Australia

[21] Appl. No.: 09/051,527
[22] PCT Filed: Nov. 14, 1996
[86] PCT No.: PCT/AU96/00717
  § 371 Date: Apr. 9, 1998
  § 102(e) Date: Apr. 9, 1998
[87] PCT Pub. No.: WO97/18466
  PCT Pub. Date: May 22, 1997

[30] Foreign Application Priority Data

Nov. 14, 1995 [AU] Australia ................. PN6536

[51] Int. Cl.[7] .................................................. E21C 35/24
[52] U.S. Cl. ................................. 299/1.1; 299/1.05
[58] Field of Search ........................ 299/1.05, 1.1, 299/1.2

[56] References Cited

U.S. PATENT DOCUMENTS

| | | | |
|---|---|---|---|
| 4,143,552 | 3/1979 | Godfrey | 299/1.05 |
| 5,090,775 | 2/1992 | Berger | 299/1.05 |
| 5,121,365 | 6/1992 | Leigh et al. | 367/118 |

FOREIGN PATENT DOCUMENTS

| | | | |
|---|---|---|---|
| 3127702 | 2/1983 | Germany | 299/1.05 |
| 0611022 | 6/1978 | U.S.S.R. | 299/1.2 |
| 0891914 | 12/1981 | U.S.S.R. | 299/1.1 |

OTHER PUBLICATIONS

Mowrey, G.L. "Promising coal interface detection methods" Mining Engineering Magazine Jan. 1991, pp134–138.

*Primary Examiner*—Eileen D. Lillis
*Assistant Examiner*—John Kreck
*Attorney, Agent, or Firm*—Smith-Hill and Bedell

[57] ABSTRACT

A mining machine (4) has a vertically movable jib (6) mounted in front of it and carrying a drum shaped drilling head (12) at its forward end. The drilling head is provided with radially projecting picks which rip coal out of a coal seam (1) located between an underburden (3) and an overburden (2). A forwardly-facing directional microphone (16) is mounted on the forward end of the machine (4) between the lines M where it can monitor the resonant frequencies of the picks. Electrical circuitry mounted on the machine controls the position of the jib (6) in accordance with the relative amplitudes of a unique set of natural resonant frequencies produced by the picks during mining.

5 Claims, 5 Drawing Sheets

DETECTING SEAM BOUNDARY USING PICK SOUND

FIELD OF THE INVENTION

THIS INVENTION relates to a method and apparatus for distinguishing a boundary between layers of compacted inert materials, such as bitumised surface of a roadway on a concrete substrate, or the boundary between a coal seam and surrounding rock in a mine. The invention is, however, broadly applicable to any apparatus which uses picks or similar mining bits to dislodge the required inert material, the picks comprising a body which is rotatably held at one end terminating at a hardened tip at the other end. Naturally the tips of the picks wear out during use, and they have to be replaced. This wear increases when the pick reaches the boundary as it is not designed to penetrate the material beyond the boundary.

STATE OF THE ART

Picks used on mining machines are usually cylindrical with cone-shaped front ends that scrape through the inert material to be mined. The particles or small rocks that are loosened by the picks fall down onto the base of a mining machine and are transported to the rear of the machine by a conveyor belt. A cacophony of sounds are generated during mining and which emanate from the material being mined, the picks, and the mining machine itself. Various attempts have been made to use changes in the amplitudes of these sounds to indicate that the picks are mining a different material as a result of crossing the boundary.

U.S. Pat. No. 4,143,552 proposes using the beam frequency of resonance of the picks, to indicate the nature of the material being mined. The patent suggests that by monitoring the amplitude of the beam resonant frequency and its harmonics one can detect movement of a cutting tool carrying the picks, into the unwanted rock surrounding a coal seam. Because of the wide range of noises generated during operation of a mining machine, the specification instructs the reader that the beam resonant frequencies should be detected by mounting a vibration transducer conducted along an arm carrying the cutting tool so that, in theory, the vibrations of the pick are transmitted through the structure of the mining machine to the transducer. As this is mounted to detect vibrations conducted along the arm, it is virtually unaffected by air-borne sounds generated by the mining process. These sounds emanate from many sources, such as the conveyor used to convey the material to the rear of the mining machine; the propulsion unit used to move the mining machine forwardly as mining progresses; the sound of fractured coal tumbling onto the conveyor section in front of the machine and, after passing through the machine, onto the conveying system behind it; the scraping sounds generated by the coal lumps as they are conveyed through the machine; the rotational drive fed to the cutting tool in which the picks are mounted; and the ripping sounds created by the dislodgment of the coal from the coalface by the action of the picks.

The teaching of the US patent is unfortunately theoretical, rather than practical, as it ignores the fact that the geometry and the relative movement of the portions of the machine through which the sounds pass, distort the amplitude of the beam resonant frequency and its harmonics so that it is varied by factors which have nothing to do with the nature of the material being cut by the pick.

OBJECT OF THE INVENTION

An object of this invention is to provide an improved apparatus and method for determining when a boundary between two layers of compacted material is encountered.

SUMMARY OF THE INVENTION

In accordance with one aspect of this invention a method of detecting when picks of a cutting head of a machine for breaking up a compacted layer stray beyond the boundary of the layers, comprises detecting in the vicinity of the head sets of predetermined air-borne sound frequencies, converting these sets of frequencies into electrical signals, filtering the electrical signals and applying correction factors to them in order to provide corrected signals corresponding to the respective amplitudes of a unique combination of frequencies making up each of the different sets, and using the relative changes of the corrected signal amplitudes to control the position of the head so that the amplitudes of the frequencies of the sets are restored to a predetermined relationship.

The frequencies of each set are determined from the different resonant frequencies of the pick. The pick has a range of natural resonant frequencies each corresponding to a different physical dimension of the pick. The strongest resonant frequencies are usually obtained from the length, the circumference and the radii of the pick. Each of these dimensions gives rise to a different natural frequency of vibration of the pick.

In accordance with a second aspect of the invention apparatus for breaking up a compacted layer of material, comprises: a head equipped with picks and rotated to bring them into ripping engagement with the layer; an arm supporting the head and moveable in order to bring it into engagement with different portions of the layer; a vehicle supporting the arm and moveable to advance the head progressively in relation to the layer; a microphone for converting air-borne sound signals produced in the vicinity of the picks into corresponding electrical signals and located adjacent the front end-portion of the vehicle; electrical circuitry for selectively amplifying predetermined sets of frequencies of the electrical signals each set corresponds to a unique set of resonate frequencies of the pick, applying to the amplified sets of electrical signals respective correction factors which correlate with the nature of the material being broken up, and computing from the amplitudes of the sets of corrected signals the position of the picks in relation to a boundary between the layer and an adjoining different material; and a controller connected to respond to the output of the electrical circuitry and for changing the position of the head to confine the action of the picks to the thickness of the layer.

As the apparatus of the invention relies on air-borne sound signals, the components of it which produce and process the electrical signals can be made and sold separately from the mining machine which does not require any physical modifications in order to adapt it to use the invention.

PREFERRED FEATURES OF THE INVENTION

Between two and twelve sets of frequencies may be used for carrying out the invention. Normally the number of sets used will, however, be three corresponding, respectively to the pick resonating at one of its beam frequencies, one of its circumferential resonant frequencies and one of its radial resonant frequencies. The number of independent resonant frequencies generated by a pick when working, will be determined largely by its dimensions and the way it is held and moved. During mining, the movement of the pick through the material being mined will be affected by the characteristics of the materials and these, in turn, will vary the amplitude of the different independent natural frequencies generated by the pick in the different modes of vibration mentioned above. Thus, by selecting more than one resonant mode of vibration, the relative amplitudes of the signals generated at the resonate frequencies can be monitored and used to signify a change in the composition of the material being mined. This enables appropriate action to be taken when the picks enter the overburden or underburden of the layer being mined or approach pockets of gas in or around the seam. The use of the invention to detect gas pockets can be an important safety aspect of the invention in mining coal, as gas pockets in a coal seam present a very dangerous hazard to operators and machines.

Preferably the microphone has directional characteristics to exclude unwanted sounds.

INTRODUCTION TO THE DRAWINGS

The invention will now be described in more detail, by way of example with reference to the accompanying diagrammatic drawings, in which.

Figure 3A:
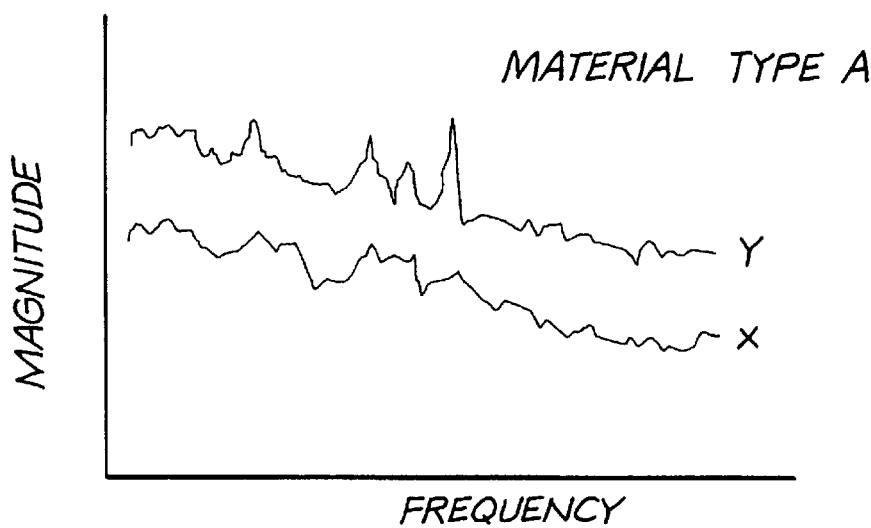
Figure 3B:
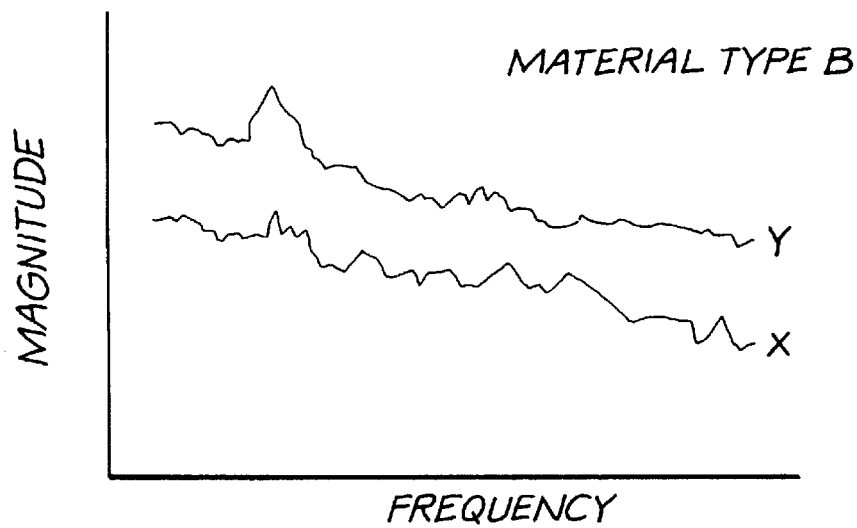
Figure 3C:
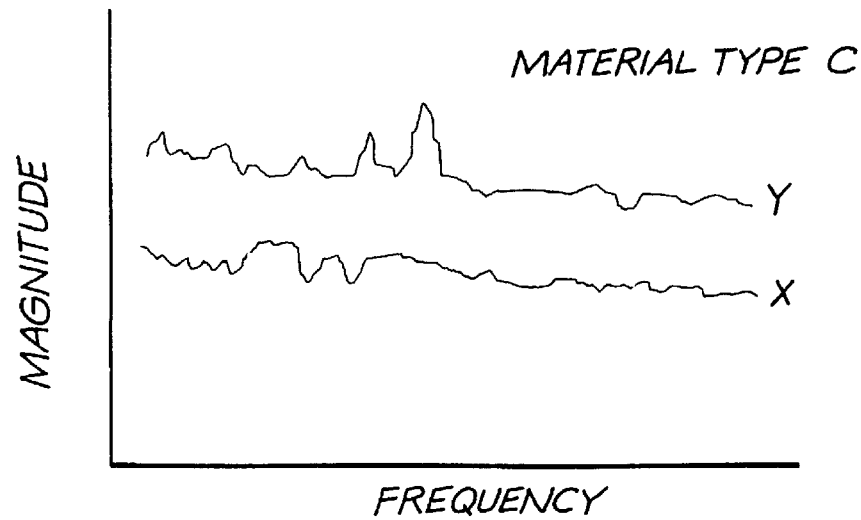
Figure 4A:
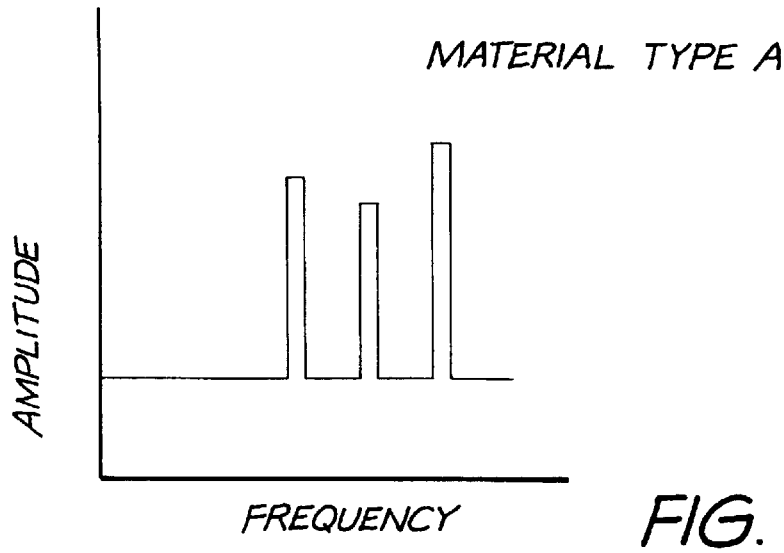
Figure 4B:
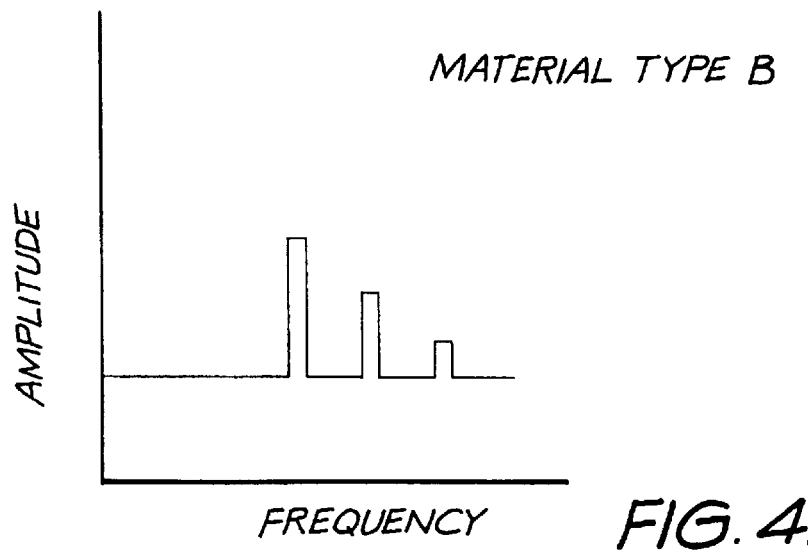
Figure 4C:
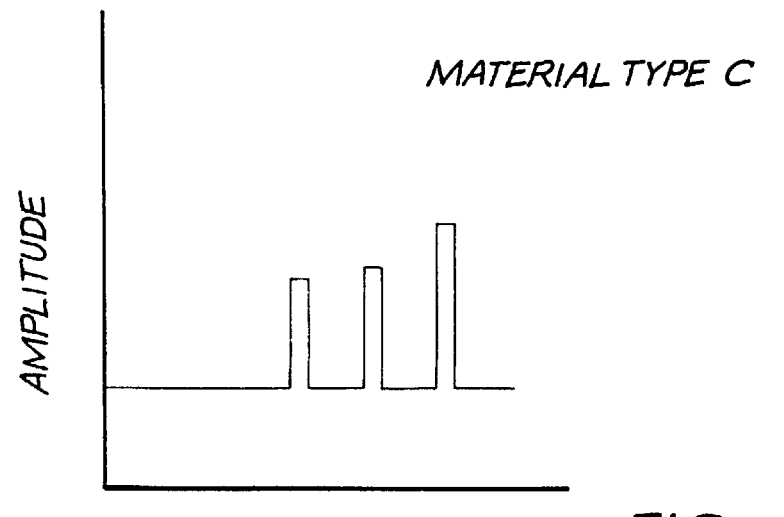
Figure 5:
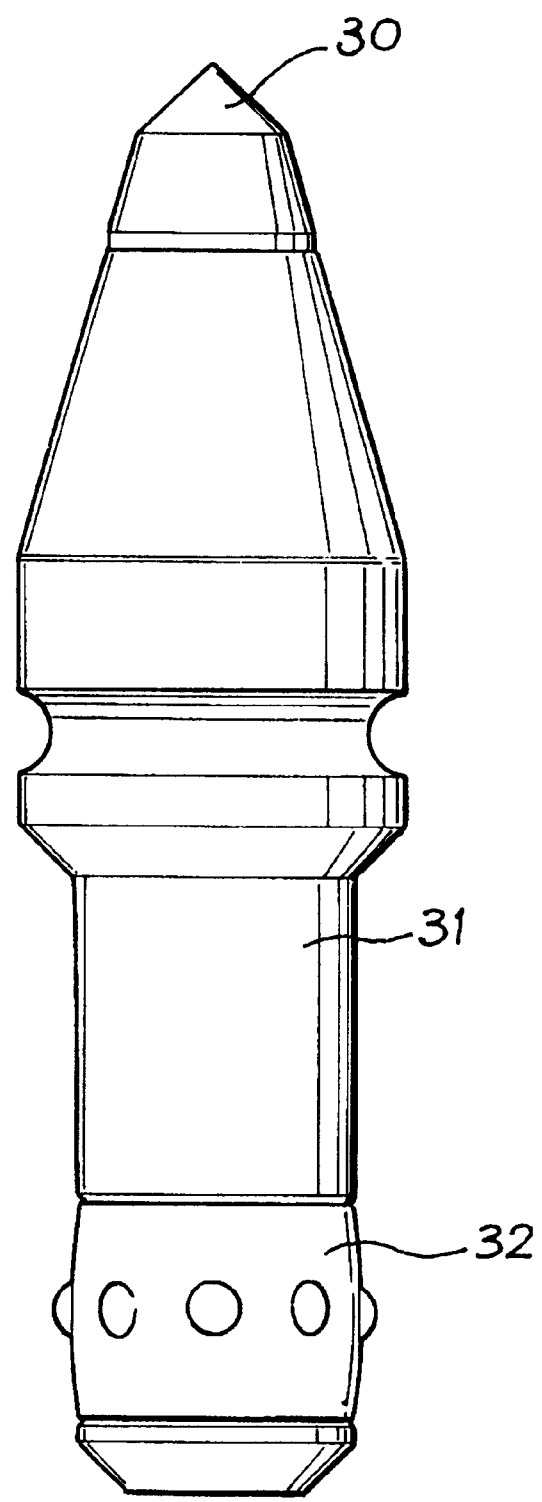

FIGS. 3A, 3B and 3C show a typical spectra of sound frequencies produced during mining, the three diagrams respectively showing the sound frequencies generated when the mining machine is cutting coal from the upper boundary, the central portion and the lower boundary of the seam, curves X showing the sound frequency spectra obtained from air-borne sound waves present in the mining chamber behind the machine and curves Y showing the sound frequency spectra obtained from air-borne sounds present at the front of the machine and near the mining head;

FIGS. 4A, 4B and 4C show, respectively, the effect on the curves Y of FIG. 3 after applying a correction process to them, using the blocked circuitry shown in FIG. 3 in order to provide a measure of the relative amplitudes of three resonant frequencies of the picks; and, FIG. 5 shows, in side view, a typical pick.

DESCRIPTION OF PREFERRED EMBODIMENT

Figure 1:
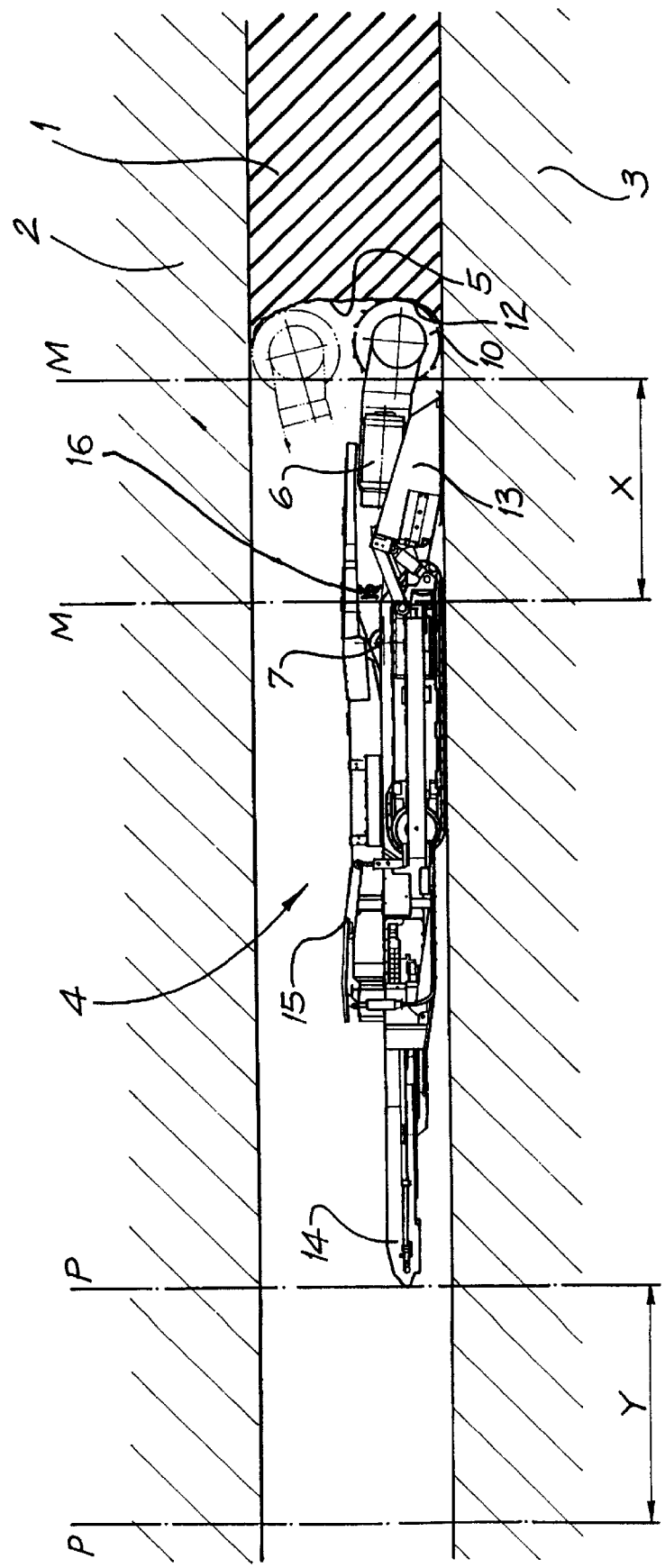
FIG. 1 is a diagrammatic side view of a mining machine working its way along an underground coal seam.

FIG. 1 shows a coal seam 1 sandwiched between an overburden layer 2 and an underburden layer 3. The seam 1 has been partially excavated by a mining machine 4 as it progressively moves towards a coalface 5 of the seam.

The mining machine 4 is equipped with a forward-extending jib 6 capable of being raised and lowered above a pivot 7 by a hydraulic mechanism (not shown) on the mining machine 4. The jib 6 carries at its forward-end a mining head 10 comprising a rotatable cylindrical drum 10 having radial removable picks 12 of the general shape shown in FIG. 5. These picks are individually mounted in collars (not shown) which allows them to rotate circumferentially. They can also vibrate longitudinally and radially during their encounter with the material being mined. A drive (not shown) from the machine 4 is used to rotate the drum 10 about a horizontal axis. As the drum rotates, the picks 12 rip coal out of the coalface 5 and propel it downwardly onto the front of a conveying section 13 which projects forwardly from the machine 4. The broken-up coal is conveyed to the rear of the machine where it is deposited onto a conveying system 14. The jib 6 reciprocates vertically to mine the coalface 5, its upper position being shown in broken outline.

As mentioned earlier a cacophony of sounds are produced when mining coal. The machine 4 carries electrical processing circuitry 15 which is connected by leads (not shown) to one or more forward-facing, directional microphones 16 mounted near the forward-end of the jib 6 between the two chain lines whose approximate positions are indicated by the letter M. The air-borne sounds produced at the coalface during excavation are detected by the microphone or microphones 16 and supplied to the circuitry 15.

FIG. 3 shows in each of the graphs 3A, 3B and 3C two curves X and Y. The curve X showed the sound spectrum obtained when the microphone 16 is located behind the miner between the two chain lines P of FIG. 1, whereas the curve Y shows the sound spectrum obtained when the microphone is repositioned between the two chain lines M in front of the mining machine 4. As is apparent from these curves, the curve X is not useable to determine the required sets of resonant frequencies to be monitored and generated by the picks, as the frequencies are masked by the other sounds produced during mining which are also air-borne. However, if a microphone able to detect air-borne frequencies is positioned in front, rather than behind, the mining machine and generally between the lines M, the curves Y are obtained and these are useable. Also, by using a directional microphone aimed towards the mining head, the wanted frequencies are picked up with greater clarity than is possible when an omni-directional microphone is used. The position of the rear line M will vary with the design of the vehicle and the sounds it produces, and will also be influenced by safety factors ensuring the microphone is not damaged during normal mining operations.

Graph B of FIG. 3 shows the spectrum obtained when the picks are exclusively mining coal, as occurs when the mining machine 4 is excavating the central thickness of the coal seam 1. The dominating sounds are the resonant sounds being generated by the picks working in the coal. There are generally at least three distinct independent resonant frequencies occurring between the frequencies of about 500 Hz and 5,000 Hz. As the head of the miner enters the overburden 2 or the underburden 3 layers, the relative amplitude of these resonant frequencies changes as also does their phase, and character. These changes are enhanced in the electrical circuitry and compared with predetermined values. This comparison allows decisions to be computed concerning the position of the mining head with regard to the boundaries of the layer being mined, and this information is then used to operate a controller (not shown) which corrects the position of the mining head to restore it to the thickness of the layer being mined.

Figure 2:
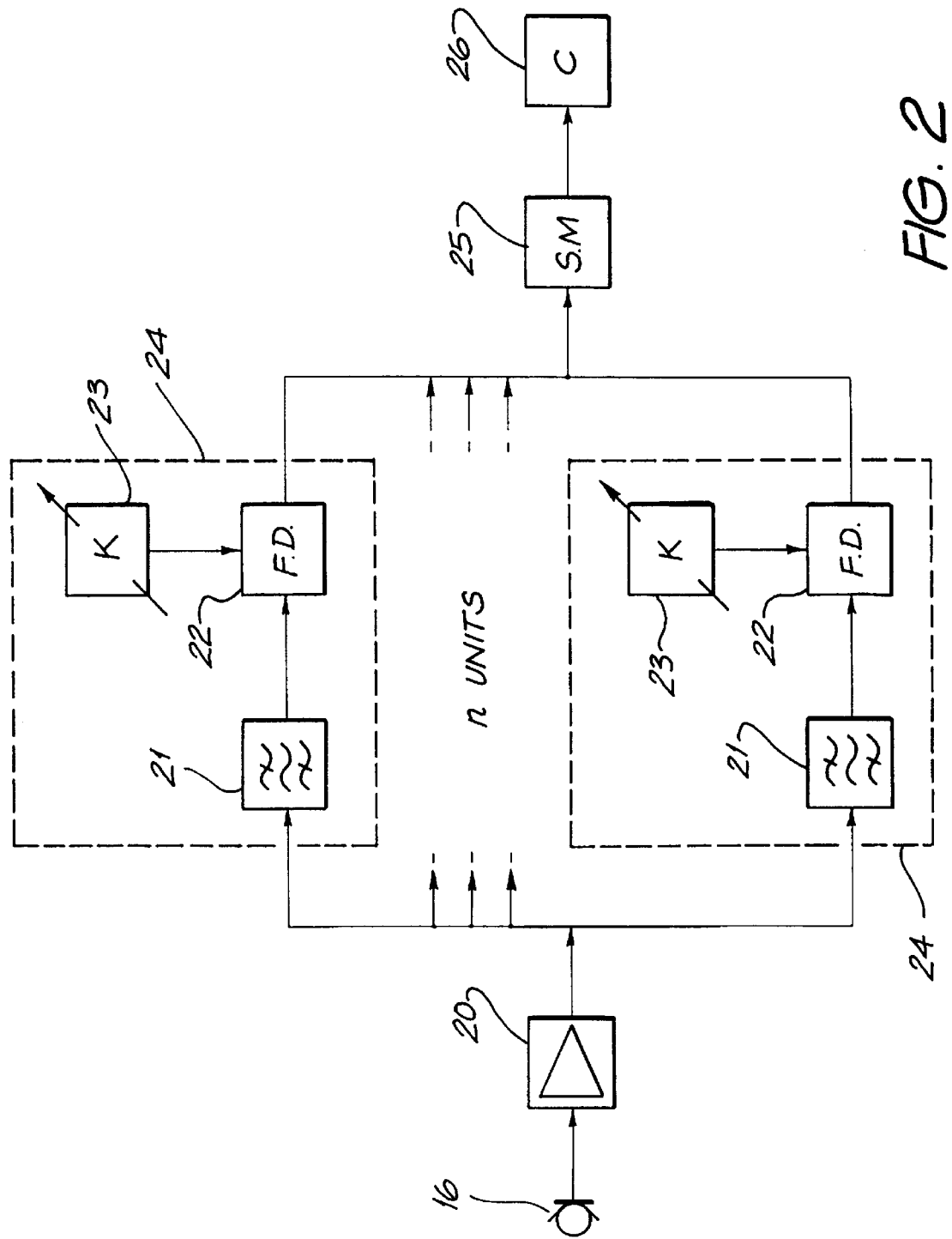
FIG. 2 is a block circuit diagram of one form of electrical circuitry useable to control the elevation of a mining head on the machine so that it stays within the confines of the coal seam being mined.

FIG. 2 shows in simplified and block schematic form the circuitry 15 for processing the information obtained from the directional microphone 16.

The electrical signals from the microphones 16 are fed to an amplifier 20 and then passed to two filter processors 24 which have at their signal entry end band-pass filters 21. These are set to pass respectively different, unique, frequencies corresponding to the different resonant frequencies of the picks. The unwanted sound frequencies are removed in each filter 21 and only the resonant frequencies are transmitted. The output of each filter 21 is supplied to a frequency discriminator 22 which selectively amplifies the specific resonant frequency required for additional processing. A function generator 23 is adjustable in accordance with the corresponding resonant frequency of the pick being used at the time. The extent of this adjustment is determined before the mining machine 4 commences work. In practice, n filter processors 24 are provided, n lying between 2 and 12. The number of processors 24 used depends on the variations in the material layers, and the types and configurations of the picks in the cutting head. The outputs of the frequency discriminators 22 of the filter processors 24 are then fed into a signal matrix 25 and associated computer, which is pre-set at a predetermined level for each of the various sets of predetermined resonant frequencies in order to provide decision-based outputs which are based upon the levels of these frequencies and their relative magnitudes with respect to one another and predetermined levels. The pre-set level of the resonant frequencies is determined empirically before mining commences. The resultant output is fed to a controller 26 which alters the position of the jib 6 to maintain the picks within the seam 1.

The output fed to a controller 26 is, amongst other things, a function of the type and age of the mining machine. The output from the controller 26, may be electrical, mechanical or hydraulic.

FIG. 5 shows, a typical mining pick. It has a cone-end 30 which penetrates the coal seam, a body shaft 31, and an end 32 which is gripped in a rotatable collar on the mining machine. During mining, the pick is shaken, jolted, rotated and vibrated by the various materials through which it is dragged. The different resonant frequencies of the pick depend on its various radii, its length and each of its circumferences. It is the monitoring of a set of these frequencies, rather than just one of them and its harmonics, coupled with the use of air-borne sounds, which distinguish this invention from the prior art teaching.

For example, when a pick encounters an interface between coal and surrounding rock, the resonant frequencies are affected by the rotation, length displacement, compression, plucking and rocking of the pick, as well as by the rattling of the pick in its holder. Each of the resonant frequencies is varied in a different manner by these effects. For instance, coal may cause the picks to slide and rotate as they pass through the coal stratum. When the picks strike sandstone, however, they vibrate and are compressed. Each of these behaviour characteristics and others, alters the different resonant frequencies differently. The number n of channels in the electrical circuit diagram of FIG. 2, are sufficient to enable all of the useful twelve resonant frequencies of the pick to be monitored, if required.

While mining is progressing, the jumble of noises produced varies to some extent with the nature of the coal being mined, ie, whether the coal is hard or soft, the nature of the overburden 2 and the underburden 3, and the position of the microphone or microphones 16. By placing a preferably directional and forwardly facing microphone between the lines M, that is to say at the front end-portion of the mining machine where it can also be protected from physical damage, and relying on air-borne sounds rather than machine borne vibrations, the masking effect of many sound sources produced by the machine is considerably reduced.

The commercial importance of being able to determine the boundaries of a coal seam is considerable. By reversing the direction of movement of the jib 6 as soon as the boundary of the seam is reached, the amount of non-carbonatious material excavated with the coal is reduced so that the quality of the coal is increased by reduction of fly ash and the load on washeries is reduced. The energy expended in inadvertently mining uncommercial overburden and underburden is saved. Finally, the working life of the picks 12 can be increased by several hundred percent in some cases, if their working can be kept within the thickness of the seam during mining.

The above described apparatus may be employed to provide the operator of the mining machine with a warning that the boundary of the coal seam has been reached. Alternatively, it may be used on a fully automated mining machine to control the direction of movement of the jib 6.

As has been mentioned above, the apparatus of the invention can be made separately from the mining machine and then fitted to it. As a simple microphone is used to detect air-borne sounds, the problems associated with rigidly fixing a transducer to the jib arm of the machine are avoided.

VARIATIONS TO THE PREFERRED EMBODIMENT

Although the apparatus has been specifically described with reference to a coal miner, it is believed that, after suitable calibration, the same principle of operation can be used for mining clay or other materials. It is not essential for the layer being mined to be sandwiched between two layers of different materials. The invention may be used to detect a boundary between two layers only. For example, it may comprise the underburden of a surface mineral deposit or a concrete foundation on which a bitumised surface layer of a road is laid. This enables a bitumised surface to be broken up, remelted and reused on the surface of the concrete without risk of damage to the concrete itself. It is also believed that the invention is applicable to any process where picks or similar bits are to be used to rip a material stratum layer adjoining another material stratum layer.

What is claimed is:

1. A method of detecting when picks of a cutting head of a machine for breaking up a compacted layer of material stray beyond the boundary of the layer, comprising:

detecting in the vicinity of the head sets of predetermined air-borne sound frequencies corresponding to resonant frequencies of the picks of the cutting head, converting these sets of frequencies into electrical signals, filtering the electrical signals and applying correction factors to them in order to provide corrected signals corresponding to the respective amplitudes of a unique combination of frequencies making up each of the different sets, wherein the correction factors are related to physical dimensions of the picks and the nature of the material being broken up, and using the relative changes of the corrected signal amplitudes to control the position of the head so that the amplitudes of the frequencies of the sets are restored to a predetermined relationship.

2. A method as claimed in claim 1, in which the number of frequencies in a set lies between two and twelve.

3. A method as claimed in claim 2, in which three frequencies are used in a set and correspond to the natural resonant frequency of a pick when vibrating axially, 4. Apparatus for breaking up a compacted layer of material, comprising:

a head equipped with picks and rotatable to bring them into ripping engagement with the layer;

an arm supporting the head and moveable in order to bring it into engagement with different portions of the layer;

a vehicle supporting the arm and moveable to advance the head progressively in relation to the layer;

a unidirectional microphone mounted in a position of safety adjacent the front end-portion of the vehicle and directed to receive signals from the head for converting air-borne sound signals produced in the vicinity of the picks into corresponding electrical signals;

electrical circuitry for selectively amplifying predetermined sets of frequencies of the electrical signals, each set corresponding to a unique set of resonant frequencies of the pick, and for applying to the amplified sets of electrical signals respective correction factors which are related to physical dimensions of the picks and the nature of the material being broken up, and for computing from the amplitudes of the sets of corrected signals the position of the picks in relation to a boundary between the layer and an adjoining different material, the electrical circuitry including a set of bandpass filters which are individually located in respective parallel signal paths of which there are between two and twelve in number, and each bandpass filter supplying its output to a frequency discriminator circuit into which a correction factor is fed so that the output of the frequency discriminator circuit reflects one of the unique natural resonant frequencies of the pick; and a controller connected to respond for changing the position of the head to confine the action of the picks to the thickness of the layer in response to the output of said electrical circuitry. radially and circumferentially.

5. Apparatus as claimed in claim 4, in which the combination of the microphone, electrical circuitry and controller is detachably mounted on the vehicle.

* * * * *